United States Patent
Waites et al.

Patent Number: 5,672,749
Date of Patent: Sep. 30, 1997

[54] PROCESS FOR PREPARING ACETYL CHLORIDE

[75] Inventors: W. Bryan Waites, St. Matthews; Robert E. Young, West Columbia; Phillip R. DeVrou, Orangeburg, all of S.C.

[73] Assignee: Albemarle Corporation, Richmond, Va.

[21] Appl. No.: 631,295

[22] Filed: Apr. 9, 1996

[51] Int. Cl.⁶ .................................................. C07C 51/58
[52] U.S. Cl. ............................................................ 562/863
[58] Field of Search .............................................. 562/863

[56] References Cited

U.S. PATENT DOCUMENTS

| | | | |
|---|---|---|---|
| 1,850,205 | 3/1932 | Hale et al. | 562/863 |
| 2,006,335 | 7/1935 | Conover | 562/863 |
| 2,475,966 | 7/1949 | Hull | 562/863 |
| 3,576,860 | 4/1971 | Zazaris | 562/863 |

FOREIGN PATENT DOCUMENTS

| | | |
|---|---|---|
| 901598 | 5/1972 | Canada . |
| 27-4567 | 11/1952 | Japan . |
| 458541 | 1/1975 | U.S.S.R. . |

*Primary Examiner*—Paul J. Killos
*Attorney, Agent, or Firm*—Philip M. Pippenger

[57] ABSTRACT

The yield of acetyl chloride from the reaction between acetic anhydride and hydrogen chloride is increased by withdrawing acetyl chloride, optionally together with at least some of the acetic acid by-product, from the reaction mixture as the reaction proceeds and recycling the remainder of the reaction mixture to the reactor for reaction with additional hydrogen chloride.

4 Claims, No Drawings

PROCESS FOR PREPARING ACETYL CHLORIDE

FIELD OF INVENTION

This invention relates to a process for preparing acetyl chloride.

BACKGROUND

As disclosed in Japanese Kokoku 27-4567 (Inoue et al.) and Soviet Certificate of Authorship SU 458541 (Salakhov et al.), it is known that acetyl chloride can be prepared by reacting acetic anhydride with hydrogen chloride in accordance with the equation:

$$(CH_3CO)_2O + HCl \rightarrow CH_3COCl + CH_3COOH$$

Inoue et al. generate their acetic anhydride reactant in situ by reacting ketene with acetic acid before allowing the ketene to contact hydrogen chloride, and they employ an excess of the acetic acid in order to provide a solvent for their subsequent reaction of equimolar amounts of acetic anhydride and HCl. After completing the reaction in a first gas-absorption tower, they distill the acetyl chloride product from the reaction mass in a second gas-absorption tower and recycle the thus-separated acetic acid to the reaction vessel.

Salakhov et al. teach that high yields of acetyl chloride are obtained when acetic anhydride and hydrogen chloride are reacted in a mol ratio of 1–5/1, preferably 4/1, in a fluidized perlite bed at a temperature of 150°–250° C.

Although these known processes are effective in preparing the desired product, the ketene route is unattractive because of its generation of numerous impurities; and none of the known processes is sufficiently economical to be desirable for commercial use.

SUMMARY OF INVENTION

It has been found that acetyl chloride can be obtained in high yield from the reaction of acetic anhydride with anhydrous hydrogen chloride at moderate temperatures without the need for a catalyst when acetyl chloride is withdrawn from the reaction mixture as the reaction proceeds and the remainder of the reaction mixture is recycled to the reactor for reaction with additional hydrogen chloride.

DETAILED DESCRIPTION

In the process of the invention, the acetic anhydride and anhydrous hydrogen chloride may be reacted in any manner that permits adequate contact between the reactants, easy withdrawal of the reaction mixture for removal of the acetyl chloride, and recycling of the remainder of the reaction mixture.

Conveniently, the process is conducted in a vessel which is provided with a packed column absorber (and with a distillation column if desired); and reaction is effected by circulating acetic anhydride maintained at a temperature of about 50°–140° C., preferably about 65°–115° C., through the absorber column while hydrogen chloride vapor is fed into the vapor space of the vessel so as to enter the absorber column in a countercurrent flow and become partially absorbed into the acetic anhydride. The acetic anhydride employed as a starting material for the reaction may be pure acetic anhydride, or it may be an impure material containing as little as 3% by weight of acetic anhydride. Most commonly, it is a solution of acetic anhydride in acetic acid or, in a commercial process, a heel from a previous reaction (a solution containing some acetyl chloride and dissolved hydrogen chloride in addition to the acetic anhydride and acetic acid) or an acetic anhydride that has been used to absorb/capture excess HCl from a previous reaction.

When this technique is used, the feed rates are not critical as long as they ensure contact with the acetic anhydride of a stoichiometric sufficiency of the hydrogen chloride. The optimum feed rates vary, of course, with the concentration of acetic anhydride in the starting material; and they also vary with the recovery technique employed, since less of the HCl feed actually reacts with the acetic anhydride to produce acetyl chloride in vessels provided with a distillation column than in vessels from which the acetyl chloride is recovered by flash distillation. Thus, although feed rates providing about 1.00–1.03 mols of HCl/mol of acetic anhydride are generally preferred in the latter situation, feed rates providing about 1.5–3.0 tools of HCl/mol of acetic anhydride may be needed in vessels provided with a distillation column. The excess HCl is captured by an acetic anhydride scrubber for recycle.

As an example, when the starting solution is a heel in which the acetic anhydride content is about 30% and the acetic acid content is about 48%, and a distillation column is utilized, excellent results (acetyl chloride purity>96% by weight) are achieved when the relative HCl/solution feed rates are about 10–15/1 on a volume basis at approximately atmospheric pressure. The use of an acetic anhydride solution having a higher or lower acetic anhydride content would require, respectively, increasing or decreasing the relative HCl/solution feed rate ratio to obtain substantially the same results; and the use of flash distillation instead of a distillation column permits essentially the same results to be obtained when the relative HCl/solution feed rate ratio is decreased.

The countercurrent circulation of the two feeds through the absorber column results in the formation of a vaporous reaction mixture containing acetic anhydride, hydrogen chloride, acetic acid, and the desired acetyl chloride. It has been found that the amount of acetyl chloride capable of being produced in an acetic anhydride/HCl reaction is limited by the reversibility of the reaction, a reaction that may be represented by the following equation:

$$(CH_3CO)_2O + HCl \rightleftharpoons CH_3COCl + CH_3COOH$$

In accordance with the present invention, it has now also been found that the conversion, or yield, of acetic anhydride to acetyl chloride in the reaction can be increased by removing at least a portion of the product during the course of the reaction to shift the equilibrium of the reaction mixture. This removal may be accomplished by any of the techniques conventionally used to separate product at the end of the reaction. As already indicated, the use of a distillation column or the use of flash distillation can be preferred—the former having the advantage of providing a purer product, and the latter having the advantage of decreasing the amount of HCl that must be fed to the reactor.

Although the equilibrium of the reaction mixture could be shifted by removing either of the products, the boiling points of the components are such as to make it more practical to remove the acetyl chloride or both the acetyl chloride and some of the acetic acid. Thus, although other temperatures in the range of about 50°–120° C. may be used, it is ordinarily preferable to maintain the overhead temperature at or slightly below 51° C. (the normal boiling point of acetyl chloride) when it is wished to ensure separation of most of the acetic acid and acetic anhydride from the acetyl chloride.

Acetyl chloride condensed from the reaction mixture is collected, and the remainder of the reaction mixture—a mixture which usually contains the unreacted acetic anhydride and small amounts of dissolved acetyl chloride and hydrogen chloride in a major amount of acetic acid—is recycled to the reactor for reaction with additional hydrogen chloride and the consequent formation of more acetyl chloride.

The invention is advantageous in that it provides an economical, commercially feasible process for preparing acetyl chloride in high yields from acetic anhydride and hydrogen chloride.

The following example is given to illustrate the invention and is not intended as a limitation thereof.

EXAMPLE

Charge a 1-liter flask with a solution of about 303 g of acetic anhydride, about 3 g of HCl, and about 224 g of acetyl chloride in about 485 g of acetic acid. Circulate the solution through a 1-inch column absorber having a height of six inches and packed with 6×6 mm Raschig rings at a rate of 30 mL/minute. Maintain the solution at 85° C. while feeding anhydrous HCl at a rate of about 400 cc/minute into the vapor space of the flask so that it enters the absorber column in a countercurrent flow and becomes partially absorbed into the solution. As the reaction proceeds, feed the vapors from the absorber column (vapors containing acetyl chloride, acetic acid, acetic anhydride, and HCl) into a 1-inch, 6-stage Oldershaw distillation column which is equipped with a cold condenser and has its reflux ratio set to maintain the vapor temperature entering the condenser at or slightly below 51° C. in order to ensure separation of most of the acetic acid and acetic anhydride from the acetyl chloride. Collect the acetyl chloride condensate at −15° C. and recycle the remainder of the reaction mixture to the absorber column for reaction with additional HCl.

When 294.03g of HCl have been fed to the system, it is found that 72.39 g have reacted with acetic anhydride—most of the remainder having been trapped at the vent of the system. Collected as distillate is a 340.66 g mixture of 96.61% by weight of acetyl chloride, 0.63% by weight of acetic anhydride, 0.65% by weight of HCl, and 1.81% by weight of acetic acid. Collected from the flask is a heel weighing about 677 g and containing 86.16% by weight of acetic acid, 7.82% by weight of acetyl chloride, 5.52% by weight of acetic anhydride, and 0.5% by weight of HCl. The yield of acetyl chloride, based on reacted HCl, is 100%.

What is claimed is:

1. In a process for preparing acetyl chloride by reacting acetic anhydride with hydrogen chloride to form a mixture of acetyl chloride, acetic acid, acetic anhydride, and hydrogen chloride in a reactor, the improvement which comprises improving the yield of acetyl chloride by withdrawing acetyl chloride from the mixture as the reaction proceeds and recycling the remainder of the mixture to the reactor for reaction with additional hydrogen chloride.

2. The process of claim 1 wherein the reaction is conducted in the absence of a catalyst.

3. The process of claim 1 wherein (a) the reaction between the acetic anhydride and the hydrogen chloride is conducted at a temperature of about 50°–140° C. so as to form a vaporous mixture of acetyl chloride, acetic acid, acetic anhydride, and hydrogen chloride, (b) the vaporous mixture is distilled at a temperature in the range of about 50°–120° C. to separate most of the acetic acid and acetic anhydride from the other components, and (c) the condensate is recycled to the reactor.

4. The process of claim 3 wherein the reaction is conducted at a temperature of about 65°–115° C.

* * * * *